US012642992B2

(12) United States Patent
Zhao

(10) Patent No.: US 12,642,992 B2
(45) Date of Patent: Jun. 2, 2026

(54) PATIENT SUPPORT APPARATUS FOR A RADIOTHERAPY SYSTEM

(71) Applicant: ELEKTA BEIJING MEDICAL SYSTEMS CO., LTD, Beijing (CN)

(72) Inventor: Weicheng Zhao, Beijing (CN)

(73) Assignee: ELEKTA BEIJING MEDICAL SYSTEMS CO., LTD, Beijing (CN)

( * ) Notice: Subject to any disclaimer, the term of this patent is extended or adjusted under 35 U.S.C. 154(b) by 153 days.

(21) Appl. No.: 18/716,852

(22) PCT Filed: Dec. 23, 2021

(86) PCT No.: PCT/CN2021/140713
§ 371 (c)(1),
(2) Date: Jun. 5, 2024

(87) PCT Pub. No.: WO2023/115440
PCT Pub. Date: Jun. 29, 2023

(65) Prior Publication Data
US 2025/0032820 A1 Jan. 30, 2025

(51) Int. Cl.
*A61N 5/10* (2006.01)

(52) U.S. Cl.
CPC ................................... *A61N 5/1049* (2013.01)

(58) Field of Classification Search
CPC .. A61N 5/1049; A61B 5/6887; A61B 6/0407;
A61B 5/055; A61G 13/02
See application file for complete search history.

(56) References Cited

U.S. PATENT DOCUMENTS

| | | | |
|---|---|---|---|
| 4,885,998 A | 12/1989 | Span et al. | |
| 6,360,385 B1 * | 3/2002 | Lewandowski | ...... A61G 7/0509 |
| | | | 5/430 |

(Continued)

FOREIGN PATENT DOCUMENTS

| CN | 101854865 A | 10/2010 |
|---|---|---|
| CN | 103533894 A | 1/2014 |

(Continued)

OTHER PUBLICATIONS

"International Application No. PCT/CN2021/140713, International Search Report dated Aug. 30, 2022", (Aug. 30, 2022), 3 pgs.

(Continued)

*Primary Examiner* — Kiho Kim
(74) *Attorney, Agent, or Firm* — Schwegman Lundberg & Woessner, P.A.

(57) ABSTRACT

Systems are disclosed for patient positioning in radiotherapy. A patient support system comprises a base (314, 328), a linear guide comprising a bearing (908,910) and an elongate bearing guide (316,410,420,902,904) arranged to guide translational motion of the bearing (908,910) along a translation axis, and a patient support surface (114,312) coupled to the base (314,328) via the linear guide, the linear guide being arranged to guide linear motion of the patient support surface (114,312) relative to the base (314,328) in a direction parallel to the translation axis. The patient support system comprises a safety guide (600) having a safety guide end adjacent to one end of the elongate bearing guide (316,410,420,902,904), wherein an open channel (610) defined by a surface of the safety guide (600) starts at the safety guide end with an open part of the channel (610) facing the translation axis, and a depth of the channel (610) tapers away from the elongate bearing guide (316,410,420, 902,904).

17 Claims, 14 Drawing Sheets

(56) References Cited

U.S. PATENT DOCUMENTS

| | | | |
|---|---|---|---|
| 7,697,971 B1 | 4/2010 | Green, Jr. et al. | |
| 7,784,127 B2 * | 8/2010 | Kuro | A61B 6/465 |
| | | | 5/616 |
| 9,974,496 B2 * | 5/2018 | Liu | A61N 5/1049 |
| 2002/0120986 A1 | 9/2002 | Erbel et al. | |

FOREIGN PATENT DOCUMENTS

| | | | |
|---|---|---|---|
| CN | 103654836 A | 3/2014 |
| CN | 206597025 U | 10/2017 |
| CN | 208492546 U | 2/2019 |
| CN | 110248604 A | 9/2019 |

OTHER PUBLICATIONS

"International Application No. PCT/CN2021/140713, Written Opinion dated Aug. 30, 2022", (Aug. 30, 2022), 5 pgs.

* cited by examiner

PATIENT SUPPORT APPARATUS FOR A RADIOTHERAPY SYSTEM

PRIORITY APPLICATIONS

This application is a U.S. National Stage Filing under 35 U.S.C. § 371 from International Application No. PCT/CN2021/140713, filed on Dec. 23, 2021, and published as WO2023/115440 on Jun. 29, 2023; the benefit of priority of which is hereby claimed herein, and which application and publication is hereby incorporated herein by reference in its entirety.

This disclosure relates to apparatus, devices, systems, and approaches for radiotherapy, and in particular but without limitation to apparatus and/or systems for patient positioning and/or support.

BACKGROUND

Radiotherapy can be described as the use of ionising radiation, such as X-rays, to treat a human or animal body. Radiotherapy is commonly used to treat tumours within the body of a human or animal patient, or subject. In such treatments, ionising radiation is used to irradiate, and thus destroy or damage, cells which form part of the tumour.

Precise control of patient position is important for effective radiotherapy. Complex patient positioning systems are used to move a patient to an intended position such that the patient can be appropriately irradiated by a treatment beam. In some systems, the patient may be translated and rotated with multiple dimensions of possible movement. In combination with treatment planning, and a moveable treatment beam, such an approach allows for the optimisation of the delivery of radiation to a tumour and can minimise the amount of healthy tissue that is exposed to radiation.

SUMMARY

An invention is set out in the claims.

FIGURES

Specific examples are now described, by way of example only, with reference to the drawings, in which.

DETAILED DESCRIPTION

Figure 1:
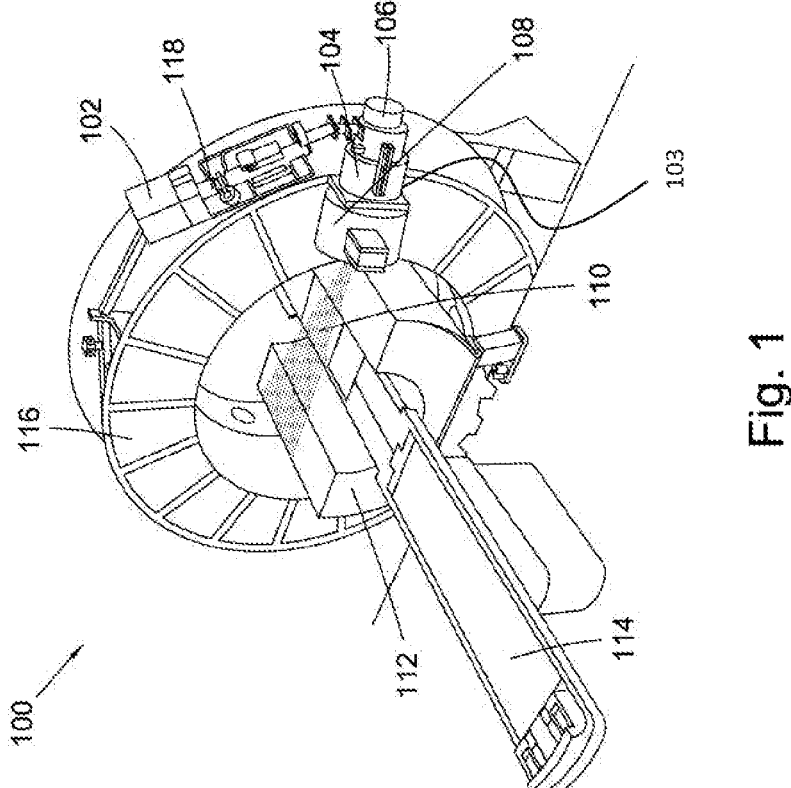
FIG. 1 shows a radiotherapy system.

FIG. 1 shows a radiotherapy system, or device, suitable for delivering, and configured to deliver, a beam of radiation to a patient during radiotherapy treatment. The device and its constituent components will be described generally for the purpose of providing useful accompanying information for the present disclosure. The device shown in FIG. 1 is in accordance with the present disclosure and is suitable for use with the disclosed systems and apparatuses. While the device in FIG. 1 is an MR-linac (magnetic resonance linear accelerator), the implementations of the present disclosure may be any radiotherapy device, for example a linac (linear accelerator) device.

The device 100 shown in FIG. 1 is an MR-linac. The device 100 comprises both MR imaging apparatus 112 and radiotherapy (RT) apparatus which may comprise a linac device. The MR imaging apparatus 112 is shown in the diagram in a partially cut away perspective manner. In operation, the MR scanner produces MR images of the patient, and the linac device produces and shapes a beam of radiation and directs it towards a target region within a patient's body in accordance with a radiotherapy treatment plan. FIG. 1 does not show the usual 'housing' which would cover the MR imaging apparatus 112 and RT apparatus in a commercial setting such as a hospital.

The MR-linac device shown in FIG. 1 comprises a source 102 of radiofrequency (RF) waves, a waveguide 104, an electron source 106, a radiation source 103, a collimator 108 such as a multi-leaf collimator configured to collimate and shape the beam, MR imaging apparatus 112 (shown partially cut away), and a patient support surface 114. In use, the device would also comprise a housing (not shown) which, together with the ring-shaped gantry, defines a bore. The patient support surface 114 is moveable and can be used to support a patient and move them, or another subject, into the bore when an MR scan and/or when radiotherapy is to commence. The MR imaging apparatus 112, RT apparatus, and a patient support surface actuator are communicatively coupled to a controller or processor. The controller is also communicatively coupled to a memory device comprising computer-executable instructions which may be executed by the controller.

The RT apparatus comprises a radiation source 103 and a radiation detector (not shown). Typically, the radiation detector is positioned diametrically opposed to the radiation source 103. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source 103 may comprise a beam generation system. For a linac, the beam generation system may comprise a source 102 of RF waves, an electron source 106 such as an electron gun, and a waveguide 104. The radiation source 103 is attached to the rotatable gantry 116 so as to rotate with the gantry 116. In this way, the radiation source 103 is rotatable around the patient so that a treatment beam 110 can be applied from different angles around the gantry 116. In a preferred implementation, the gantry is continuously rotatable. In other words, the gantry can be rotated by 360 degrees around the patient, and in fact may continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via a circulator 118 and is configured to pulse radiofrequency waves into the waveguide 104. Radiofrequency waves may pass from the source 102 of radiofrequency waves through an RF input window and into an RF input connecting pipe or tube. The electron source 106 is also coupled to the waveguide 104 and is configured to inject electrons into the waveguide 104. In the electron source 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the source 102 of radiofrequency waves, the electron source 106 and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The radiation source 103 is configured to direct the treatment beam 110 of therapeutic radiation toward a patient positioned on the patient support surface 114. The radiation source 103 may therefore also be referred to as a therapeutic radiation source. The radiation source 103 may comprise a heavy metal target towards which the high energy electrons exiting the waveguide are directed. When the electrons strike the target, X-rays are produced in a variety of directions. A primary collimator may block X-rays travelling in certain directions and pass only forward travelling X-rays to produce the treatment beam 110. The X-rays may be filtered and may pass through one or more ion chambers for dose measuring. The beam can be shaped in various ways by beam-shaping apparatus, for example by using the multi-leaf collimator 108, before it passes into the patient as part of radiotherapy treatment.

In some implementations, the radiation source 103 is configured to emit either an X-ray beam or an electron particle beam. Such implementations allow the device to provide electron beam therapy, i.e. a type of external beam therapy where electrons, rather than X-rays, are directed toward the target region as the therapeutic radiation. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The patient support surface 114, and patient, can then be moved inside the bore, to the second position, in order for the patient to be imaged by the MR imaging apparatus 112 and/or imaged or treated using the RT apparatus. The bore may hence lie about a portion of space that is suitable for receiving at least a portion of a patient—a patient receiving space. The movement of the patient support surface is effected and controlled by a patient support surface actuator, which may be described as an actuation mechanism. Together, these components may be described as a patient positioning system, which may comprise other components. The actuation mechanism is configured to move the patient support surface in a direction parallel to, and defined by, the central axis of the bore. The terms subject and patient are used interchangeably herein such that the patient support surface can also be described as a subject support surface. The patient support surface may also be referred to as a moveable or adjustable couch or table.

The inventors have appreciated that the mechanisms used in such patient positioning systems may present a finger trap risk whereby hands or fingers can become entangled, pinched, or held in the system and pressed, or crushed, between parts of the system, causing pain and/or injury. Furthermore, typical patient positioning systems are configured to move automatically in response to computer instructions, which can mean that a person positioned near the system has a reduced possibility of halting motion of the system in a finger trap scenario.

The radiotherapy apparatus/device shown in FIG. 1 also comprises MR imaging apparatus 112. The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such an MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus; and a subject support surface processor which controls the operation and actuation of the patient support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

Figure 2:
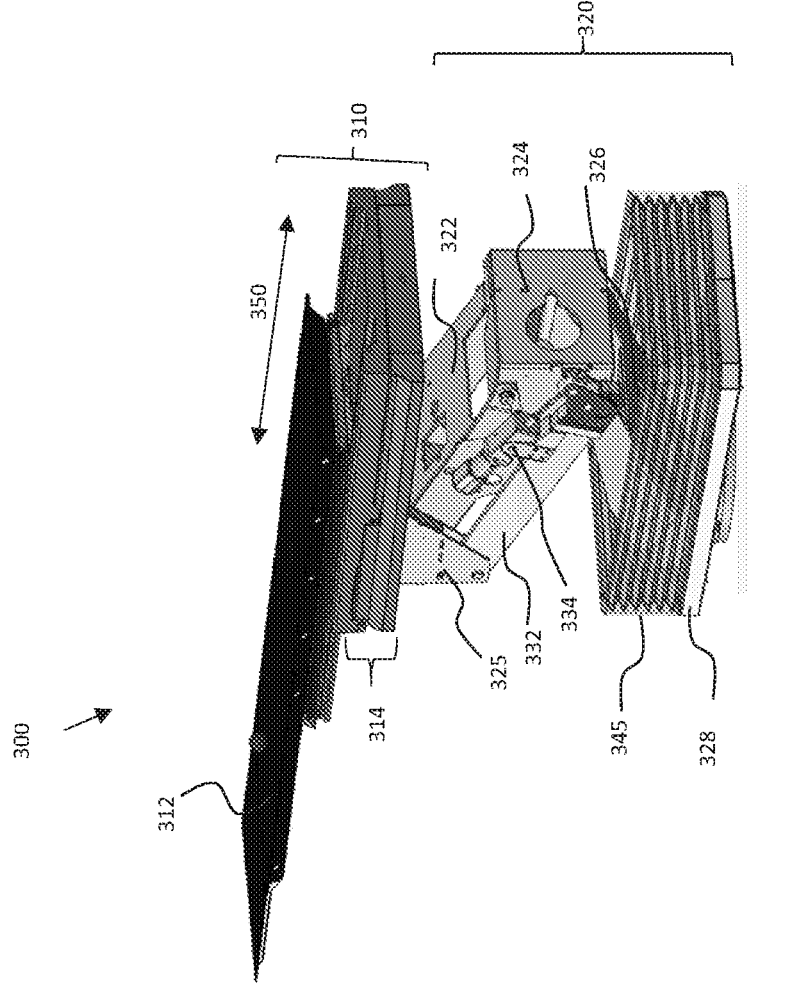
FIG. 2 shows a patient positioning apparatus in a first configuration.
Figure 3:
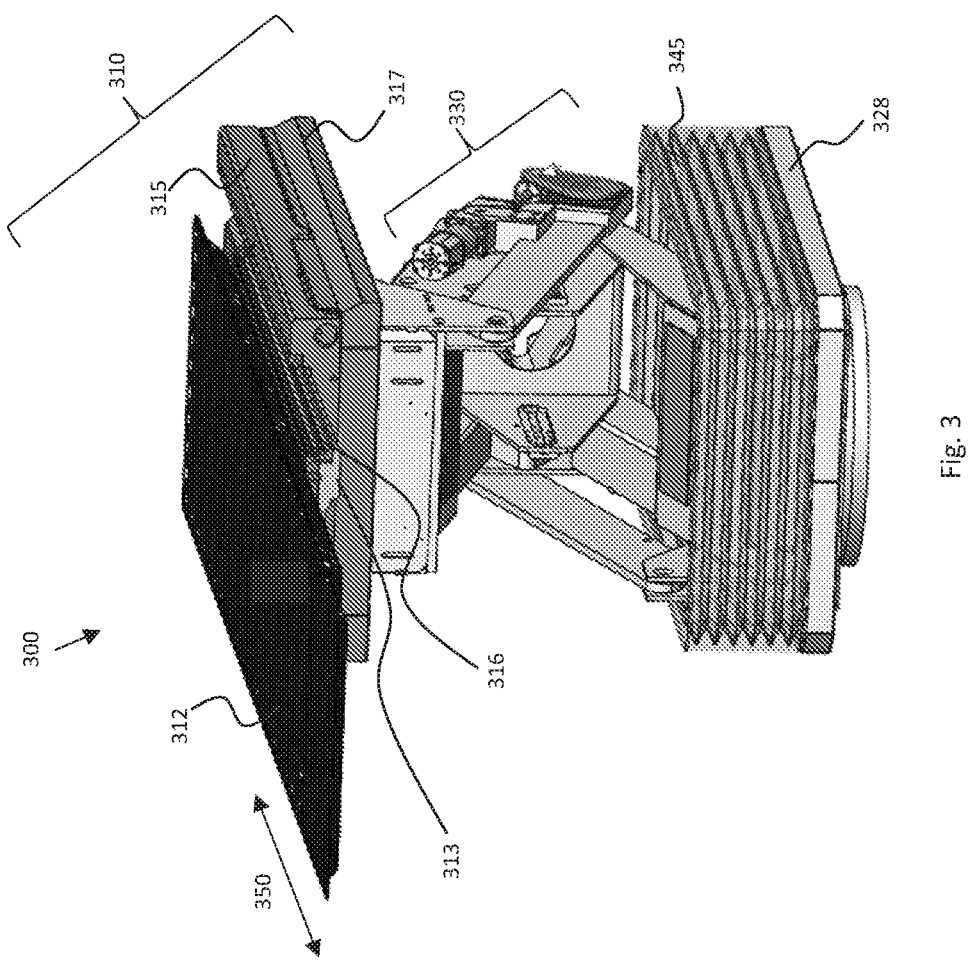
FIG. 3 shows the patient positioning apparatus of FIG. 2 in a second configuration.

FIG. 2 and FIG. 3 show a patient positioning apparatus 300. FIG. 2 shows an angled rear view of the patient positioning apparatus 300. FIG. 3 shows an angled front view of the positioning apparatus 300. The patient positioning apparatus 300 comprises a patient support apparatus 310 and a support structure 320. The support structure 320 is configured to support the patient support apparatus 310 above a floor, such as the floor of a treatment room. The support structure 320 may be configured to provide this support, in part, by means of a base 328 which contacts the floor, and/or which is embeddable within the floor. In the implementation depicted in FIGS. 2 and 3, the support structure comprises a first, or upper, supporting leg 322, a support element 324, and a second, or lower, supporting leg 326.

The patient positioning apparatus 300 also comprises a rotation mechanism. The rotation mechanism is configured to tilt, i.e. rotate, the patient support apparatus 310. The rotation is made with respect to a horizontal plane, or equivalently with respect to the floor of the treatment room, in order to adjust a tilt angle, for example a pitch angle. In the implementation shown in FIGS. 2 and 3, the rotation mechanism comprises a drive member 332 and an actuation mechanism 330. The rotation mechanism may also comprise a coupling element 325 which couples the drive member 332 to the patient support apparatus 310. The rotation mechanism is configured to impart a force, via the drive member 332, to an underside of the patient support apparatus 310 to thereby rotate the patient support apparatus 310 with respect to the support structure 320.

The patient support apparatus 310 is configured to support a patient. The patient support apparatus 310 comprises a patient support surface 312 and a patient support base 314. In use of the apparatus, a patient may lie on the patient support surface 312. In other words, in use, the patient contacts an upper surface of the patient support apparatus 310. The patient support surface 312 is coupled to the patient support base 314 using a linear guide. As will be known to those skilled in the art, a linear guide is arranged to hold two components relatively rigidly with respect to each other via a coupling mechanism that allows translational motion of the components relative to each other back and forth along a particular axis but will prevent lateral and/or twisting motion of the two components relative to one another. The patient support surface 312 can be moved linearly with respect to the patient support base 314 along a direction parallel with the longitudinal axis of the patient support apparatus 310. The directions of this linear movement are indicated by the double-headed arrow 350. Movement of the patient support surface 312 with respect to the patient support base 314 is controlled via a linear actuator.

As can be seen in FIG. 3, a supporting structure 315 of the patient support base 314 is coupled to an intermediate support structure 313 of the patient support surface 312 via the linear guide. As will be appreciated by those skilled in the art, the coupling shown in FIGS. 2 and 3 may be considered as a single linear guide or as two linear guides. The linear guide comprises an elongate bearing guide 316 that is mounted to the intermediate support structure 313. In some examples, an elongate bearing guide is instead mounted to the supporting structure 315 and in other examples, an elongate bearing guide is mounted to each of the intermediate support structure 313 and the supporting structure 315. Likewise, more than one pair of elongate bearing guides may form the linear guide. At least one bearing is provided to move relative to the elongate bearing guide, enabling the linear movement. The bearing may be mounted or attached to one of the supporting structure 315 or the intermediate support structure 313, or may not be mounted or attached to either the supporting structure 315 or the intermediate support structure 313—as may be the case when the system is being assembled, disassembled, or tested. Whichever arrangement is used, the respective components allow the patient support surface 312 to be coupled to and linearly translated relative to the patient support base 314.

Separate to the linear guide described above, the patient positioning apparatus 300 may be configured to rotate the patient support surface 312 with respect to one or both of a pitch and a roll rotation axis. In such an implementation, the axis of linear movement of the patient support surface 312 with respect to the patient support base 314 may be parallel with the roll rotation axis. In alternative implementations, the axis of linear movement of the patient support surface 312 with respect to the patient support base 314 and the roll rotation axis may not be parallel. The roll rotation movement and/or the pitch rotation movement may be controlled via a linear actuator or suitable actuation mechanism 330.

In addition, or as an alternative, to a longitudinal movement, the patient positioning surface may also be configured to move laterally. This movement may be perpendicular to the longitudinal movement and can be controlled via movement of the supporting structure 315 with respect to a lateral sledge 317. This movement can be effected by actuators in a known way, and may also make use of one or more linear guides. In summary, the patient support surface 312 may be configured to move in any, all, or a combination of three translator degrees of freedom: height, a longitudinal movement and a lateral movement.

The support structure 320 is configured to bear the weight of the patient support apparatus 310, as well as a patient positioned on the patient support surface 312. Multiple implementations of the support structure 320 are envisaged. In the implementation depicted in FIGS. 2 and 3, the support structure 320 comprises an upper element coupled to an underside of the patient support apparatus 310, and a lower element coupled to the base. The upper element may be a first supporting leg 322 and the lower element may be a second supporting leg 326 coupled to the base. The first supporting leg 322 and second supporting leg 326 are coupled to one another via a support element 324. The support element 324 may be referred to as a support block or anchor element herein.

The patient support apparatus 310 is rotationally coupled to the support structure 320 to allow rotation about a rotation axis. In a simple implementation, the support structure 320 may be coupled to the patient support apparatus 310 via an interface between a shaft and one or more bearings which receive the shaft. For example, the one or more bearings may be mounted to an underside of the patient support apparatus 310, and configured to receive a shaft which forms part of the support surface. For example, an upper region of the first supporting leg 322 may culminate in a double-ended shaft, with each end of the shaft being received in a bearing mounted to a base of the patient support apparatus 310. In this implementation, the orientation of the shaft and bearings defines an axis of rotation about which the patient support apparatus 310 may rotate with respect to the support structure 320. Other implementations include a ball-joint, or any other mechanical connection that allow rotation of the patient support apparatus 310 with respect to the support surface via a rotation axis.

A second, or lower, supporting leg is coupled to the base 328. The second supporting leg 326 may be fixedly attached to the base 328. Alternatively, the coupling may be achieved via a lower coupling element and the second supporting leg 326 may be configured to rotate with respect to the lower coupling element as part of a height adjustment mechanism. The lower coupling element extends upward away from the base 328, allowing the second supporting leg 326 to be coupled to the lower coupling element. Such an arrangement defines a rotation axis parallel with the rotation axis about which the patient support apparatus 310 rotates with respect to the first supporting leg 322.

The support structure 320 may also comprise a height adjustment mechanism (not shown in the figures). The height adjustment mechanism is configured to adjust the height, i.e. vertical distance, of the patient support apparatus 310 above the floor or base. The height adjustment mechanism comprises one or more motor mechanisms. An upper motor mechanism may be positioned within, form part of, and/or be coupled to, the support element 324. A lower motor mechanism may be positioned within, form part of, and/or be coupled to, the lower coupling element.

The height adjustment mechanism may be formed by one or multiple different mechanisms. In the implementation shown in FIG. 2 and FIG. 3, the height adjustment mechanism is configured to adjust the vertical distance between the support element 324 and the patient support apparatus 310 by actuating rotation of the first supporting leg 322 relative to the base 328. Thereby, the height of the patient support apparatus 310 above the floor is increased. The height adjustment mechanism comprises a rotational mechanism or motor configured to produce a rotary motion of the first supporting leg 322 with respect to the support element 324. This may be a rotary hydraulic motor. This rotary motor is housed within the support element 324. It will be appreciated that by rotating the first supporting leg 322 clockwise from the perspective shown in FIG. 2, the height of the patient support apparatus 310 above the floor/base is increased.

Optionally, an additional rotary motor may be provided. This rotary motor may be referred to as a 'lower' rotary motor in contrast to the 'upper' rotary motor described above. The lower rotary motor is also housed within the support element 324 and is configured to drive rotation with respect to the support element 324 and the lower leg 326.

The height adjustment mechanism may thereby also be configured to adjust the vertical distance between the support element 324 and the base 328 and/or floor of the treatment room, by actuating the second supporting leg 326 using this lower rotary motor. Thereby, the height of the patient support apparatus 310 is adjusted. By synchronously driving rotation using both the upper and the lower rotary motor, the vertical height of the patient support surface 312 may be adjusted.

For example, the height adjustment mechanism may comprise a lower rotational mechanism or motor, e.g. a rotary hydraulic motor, configured to produce a rotary motion of the second supporting leg 326 with respect to the support structure 324. It will be appreciated that by rotating the second supporting leg 326 anti-clockwise, from the perspective shown in FIG. 2, the height of the patient support apparatus 310 above the base is increased.

The height adjustment mechanism is configured to control a height of the patient support apparatus 310 above the floor of the treatment room. As described above, the patient support apparatus 310, and in particular the base of the patient support apparatus 310, is rotationally coupled to the support structure 320 to allow rotation about a rotation axis. By adjusting the height of the patient support apparatus 310 above the floor of the treatment room using the height adjustment mechanism, the height of this rotation axis can also be adjusted.

Described herein is a support structure 320 and height adjustment mechanism which comprises a mechanism capable of rotating one or a plurality of supporting legs about rotation axes in order to adjust the height of the patient support apparatus 310. However, the height adjustment mechanism may take multiple forms. For example, the height adjustment mechanism may comprise an arrangement of hydraulic pistons positioned and configured to adjust the height of the patient support apparatus 310. An alternative implementation may involve a scissor lift mechanism. The skilled person will be aware of other possible ways in which the height of a patient support apparatus 310 may be adjusted. Regardless of the specific implementation of the support structure 320 and/or height adjustment mechanism, the rotation mechanism is coupled to the support structure 320 and is configured to impart a force to an underside of the patient support apparatus 310 in order to rotate the patient support apparatus 310 with respect to the support structure 320.

In some implementations, the positioning apparatus 300 also comprises a skirt 345 (configured to cover the support structure 320 and rotation mechanism). The skirt 345 is connectable between the base 328 and the patient support apparatus 310. The skirt 345 has a flexibility, and in particular may have a concertina configuration, i.e. be configured to extend, compress, or collapse in folds like those of a concertina. Thus, patients and clinicians are protected from possible injury due to the moving mechanisms described herein. It is simpler to provide this protection using a simple skirt 345 by virtue of the present design, and in particular by virtue of the rotation mechanism being attached to and supported by the support structure. In FIG. 2 and FIG. 3, the skirt 345 is shown as folded or compressed down away from the patient support apparatus 310 so that the support structure 320 and rotation mechanism can be seen.

Figure 4:
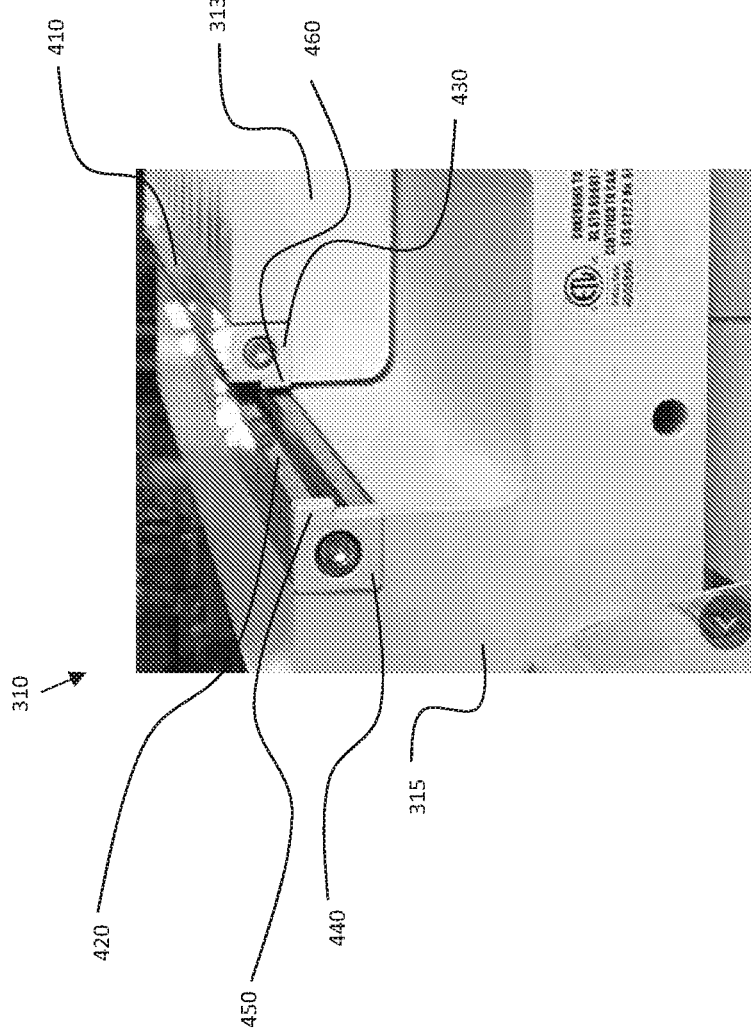
FIG. 4 shows a linear guide for a patient positioning apparatus.

FIG. 4 shows a close-up perspective of part of the patient support apparatus 310. The intermediate support structure 313 of the patient support surface 312 and the supporting structure 315 of the patient support base 314 are shown. As described above, the intermediate support structure 313 is coupled to the supporting structure 315 via a linear guide. The linear guide comprises a bearing and an elongate bearing guide. In FIG. 4, the bearing is held between a first elongate bearing guide 410 mounted to the intermediate support structure 313 and a second elongate bearing guide 420 mounted to the supporting structure 315. Each elongate bearing guide has a guide surface which is arranged to contact the bearing such that the bearing can move along it. In other examples, the linear guide comprises only one elongate bearing guide, the elongate bearing guide having a guide surface. The linear guide is arranged to guide translational motion of the bearing along a translation axis and thereby to guide linear motion of the patient support surface relative to the base in a direction parallel to the translation axis. Coupling the patient support surface 312 to the patient support base 314 via the linear guide allows the patient support surface 312 to be translated back and forth in a direction parallel to the elongate bearing guides 410, 420.

The intermediate support structure 313 has an end stop 430 positioned at an end of the first elongate bearing guide 410 in the longitudinal direction. Likewise, the supporting structure 315 has an end stop 440 positioned at an end of the second elongate bearing guide 420 corresponding to the end of the first elongate bearing guide 410 having the end stop 430. The end stop 440 of the supporting structure 315 extends in a direction perpendicular to the longitudinal direction of the second elongate bearing guide 420, and extends beyond the second elongate bearing guide 420 such that, when the intermediate support structure 313 is moved towards the end stop 440, there is a point at which the bearing will contact the end stop 430 and the intermediate support structure 313 will accordingly be prevented from traveling any further in that direction. The end stop 440 therefore may act as a limit to the extent of translation that the patient support surface 312 can undergo in a particular direction and provides a stopping interface that helps to prevent the patient support surface 312 from translating too far and, for example, becoming decoupled from the patient support base 314. In other examples, the end stop 430 of the first elongate bearing guide 410 may press against the end stop of the second elongate bearing guide 420 to provide a further stopping effect.

The two end stops 430, 440 are shaped such that together they form a cover that conceals the linear guide components from external viewing or interference from that end of the linear guide. In FIG. 4 each end stop has a face that has a corresponding tab portion 450, 460 that protrudes outward in a direction perpendicular to the direction of motion such that, when placed adjacent to each other, the tabs 450, 460 align and the end stops together present a rectangular face that faces outward from the linear guide, providing a cap or cover to the linear guide.

In some examples, there is an end stop at each end of the one or more elongate bearing guides and each end stop helps to stop and/or prevent over-extension of the movement of the patient support surface 312 in each respective direction.

Whichever arrangement of end stops is used, a finger trap risk is present between each side of the coupled linear guide.

Figure 5:
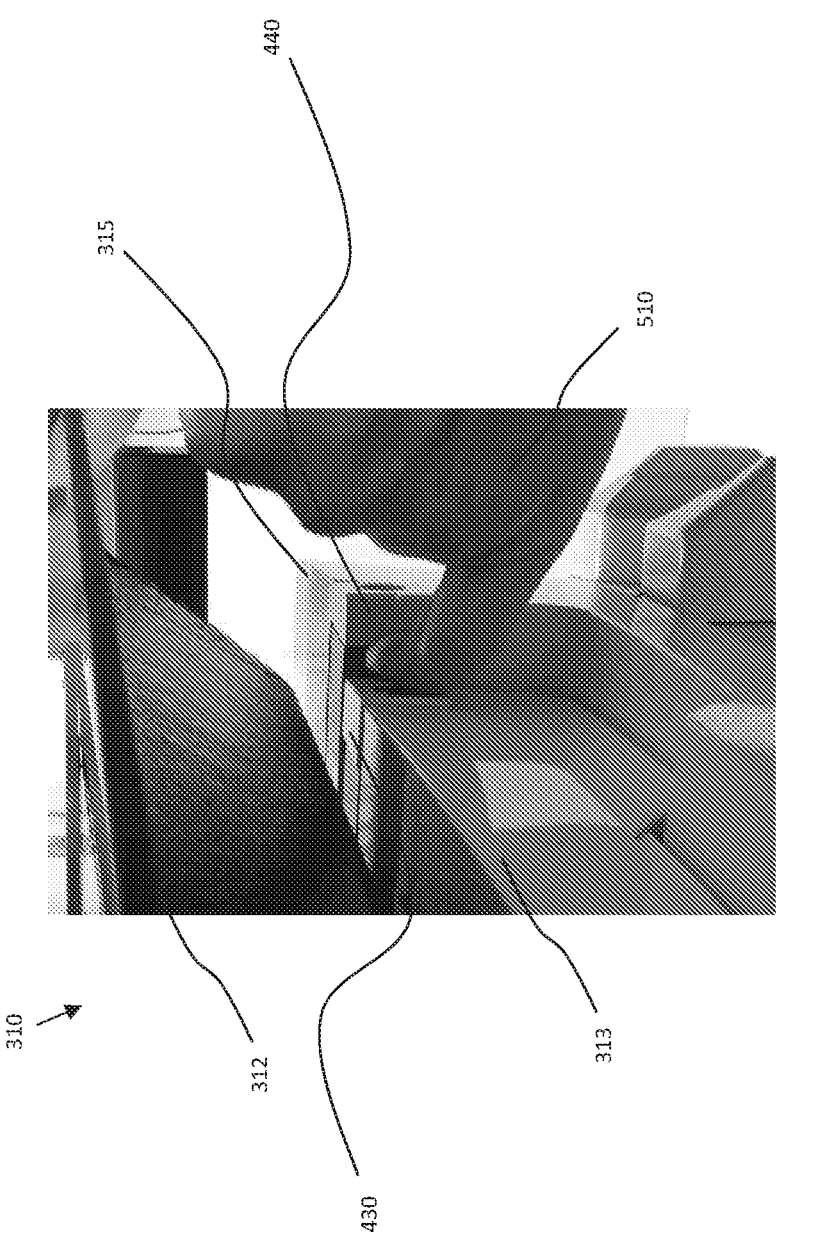
FIG. 5 shows a linear guide for a patient positioning apparatus.

FIG. 5 shows an example of a finger trap event that can occur during handling of the patient support apparatus 310. A hand 510 of a clinician, technician, or patient is positioned near to the end stop 440. The patient support surface 312 is set or programmed to move towards the end stop 440. In such a scenario, if any finger or appendage of the hand 510 is located in an inappropriate area between the two end stops 430, 440, the finger may become trapped by, entangled in, or crushed by, the patient support apparatus 310, causing potentially serious injury. Part of the hand 510 may be crushed between the inner surface of the end stop 440 that is facing towards the linear guide and the outer surface of the end stop 430 that is facing outward from the linear guide. In particular, if each end stop features a tab portion that extends or protrudes outward in a direction perpendicular to the direction of motion, as is shown in FIGS. 4 and 5, a finger or appendage may be trapped by a protruding tab portion during motion of the patient support surface 312.

Figure 6:
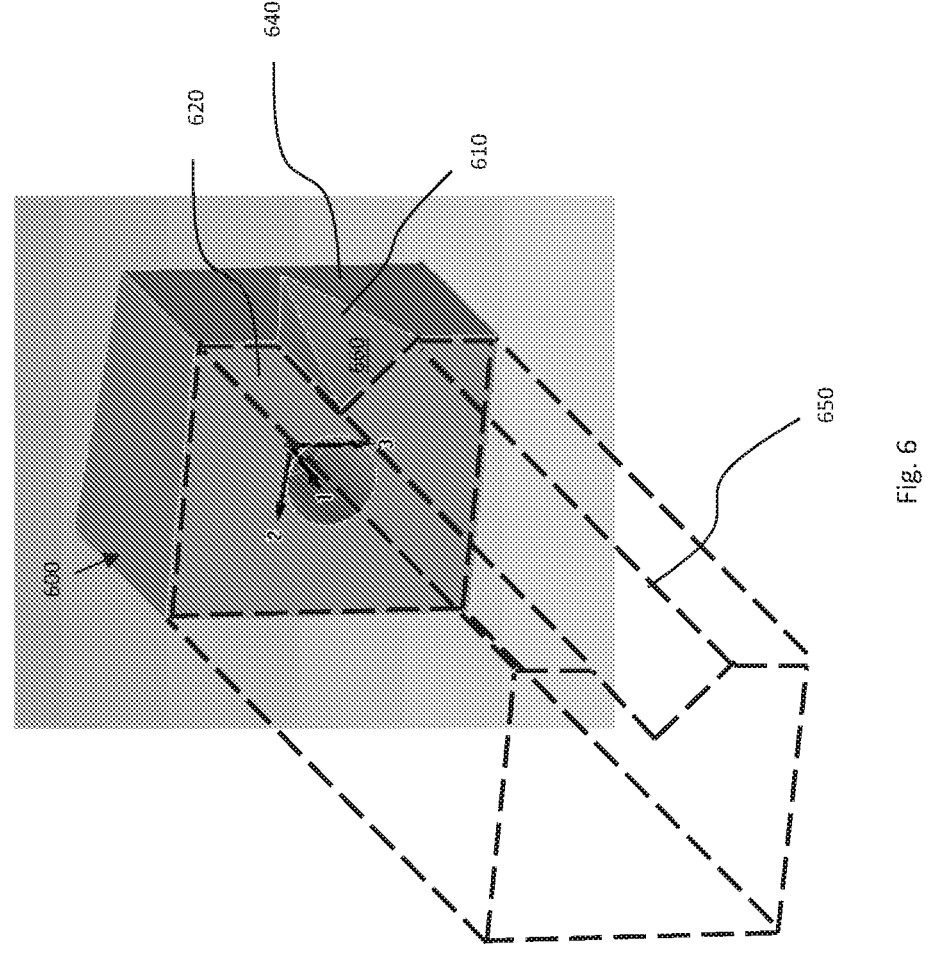
FIG. 6 shows a safety guide for a patient positioning apparatus.

FIG. 6 shows a safety guide 600 that can be used to reduce or remove the risk of finger trapping associated with the linear guide.

The safety guide 600 may be used in place of either or both of the end stops 430, 440 of FIGS. 4 and 5. In this example, the safety guide 600 has an overall cube-like shape similar to the end stops 430, 440 of FIGS. 4 and 5. FIG. 6 shows three axes labelled 1, 2, and 3. Axis 1 is parallel to the directions of translational motion of the linear guide. The safety guide 600 comprises an open channel 610. A length of the open channel 610 runs between a first face 620 of the cube-like shape of the safety guide 600 and a second face on the opposite side of the safety guide 600 (second (far) face not shown in FIG. 6). The two faces intersect axis 1 at a perpendicular angle such that the open channel 610 runs in the direction of the axis 1, the second face being separated from the first face by another face 640 that is arranged perpendicular to the axis 2. The open channel 610 thus faces the translation axis of the linear guide. The open channel 610 is thus defined by a surface of the safety guide 600. The safety guide 600 may be a guide block. Although a cube-like example is described herein, the safety guide 600 need not be cube-like in shape and other shapes may be used, such as a spherical shape featuring an open channel like that of open channel 610.

The open channel 610 has a depth in a direction parallel to the axis 2, the depth being relative to the face 640 into which the open channel 610 is set. The depth is measured from the surface of the face 640 in a direction running perpendicular to the face 640 and into the open channel 610. The depth of the open channel 610 varies along the length of the open channel 610. In the example of FIG. 6, the open channel 610 varies in width along its length, with the width being defined as the width of the open channel 610 at the surface of the face 640 into which it is set, where the width is defined in a direction parallel to the axis 3. Hence, the depth, width, and length of the open channel 610 correspond respectively to axis 2, 3, and 1 in FIG. 6. In other examples, one or more of the dimensions of the open channel 610 may not be exactly parallel to the axes 1, 2, or 3.

In some examples the open channel 610 may have a constant width along its length. In other examples, the profile of the open channel 610 may vary from that shown in FIG. 6, and several alternative cross-sectional profiles are possible. The depth of the open channel 610 may taper, reducing in depth along a direction parallel to the translation axis of the linear guide with which the safety guide 600 is associated. The depth of the open channel 610 may taper to nothing. For example, as shown in FIG. 6, the depth and width of the open channel 610 tapers to nothing as it approaches the edge of the face 640 that meets the far face of the safety guide 600 in the direction of axis 1. Alternatively, the open channel 610 may have a profile that intersects the far face with a particular width and depth, such as is shown for the near face 620 in FIG. 6. The depth of the open channel 610 may be constant. In each example the width of the open channel 610 may vary or may be constant. The width of the open channel 610 may vary by tapering and may taper away such that it reduces in size along a direction parallel to the translation axis of the linear guide and running away from the linear guide to which the safety guide 600 is to be mounted. A tapering in a particular dimension may taper linearly or it may taper non-linearly. In some examples, the open channel 610 is shaped as a groove, preferably a V-shaped groove. In other examples, the open channel 610 may have curved sides rather than straight V-shaped sides. In some examples, the depth and/or width of the open channel may increase along a particular direction before then beginning to decrease or taper along that same direction.

FIG. 6 also shows a volume 650 outlined by dashed lines that represents an elongate bearing guide in situ next to the safety guide 600, which may be one of the elongate bearing guides of FIGS. 4 and 5. The face 620 adjacent to the elongate bearing guide may be referred to as a safety guide end. The open channel 610 may be considered to start at the safety guide end.

In some examples, the open channel 610 is shaped such that when the safety guide 600 is fixed alongside one of the elongate bearing guides of the linear guide of FIGS. 4 and 5, the open channel 610 aligns with the elongate bearing guide and, in particular, a surface 660 of the open channel 610 aligns with the guide surface of the elongate bearing guide. The surface of the open channel 610 and the guide surface aligned in this way may form a continuous elongate opening, or a channel, or a groove, running in a direction parallel to axis 1. In some examples, such as that shown in FIG. 6, the surface of the open channel 610 has substantially the same cross-sectional profile as the guide surface at the end of the guide surface that is closest to the safety guide 600.

Although many alternative profiles are available for the open channel 610, preferably the profile is suitable for guiding a finger (including a thumb) or other body part in a particular direction. The safety guide 600 may hence be considered to be a guide for guiding a finger. To avoid a finger trap situation such as that shown in FIG. 5, the safety guide 600 can be used in place of one or both of the end stops 430, 440 of FIG. 4 and FIG. 5. Each safety guide 600 is positioned so that the face 640 featuring the open channel 610 faces inwards towards the opposite elongate bearing guide. Furthermore, the profile of the open channel 610 is sufficiently small in the face of the safety guide 600 that faces away from the linear guide in the direction of axis 1 that the safety guide 600 still provides a cap or cover to the linear guide, similar to the end stops 430, 440 of FIGS. 4 and 5.

Figures 7, 8:
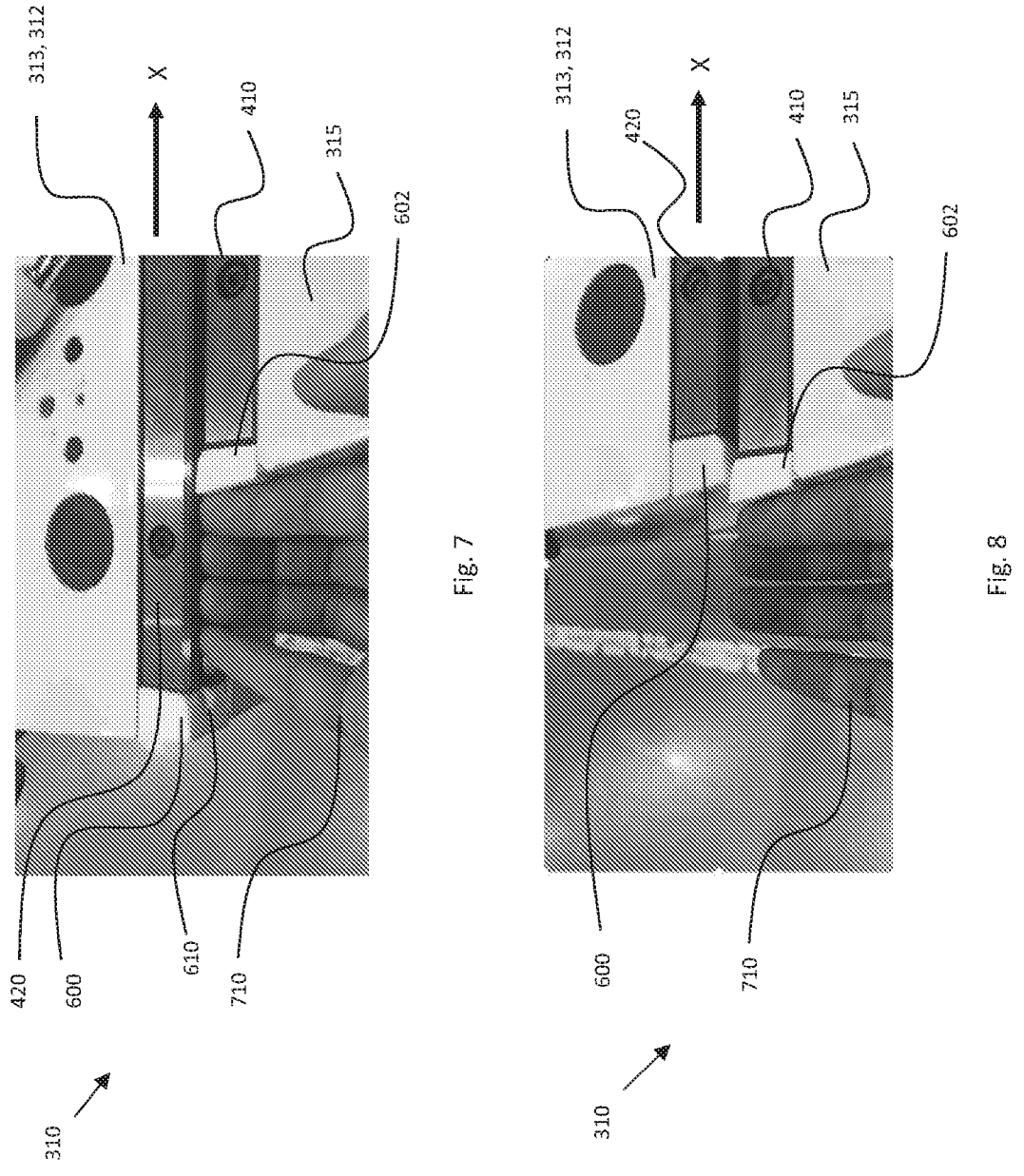
FIG. 7 shows a linear guide for a patient positioning apparatus in a first configuration.
FIG. 8 shows the linear guide of FIG. 7 in a second configuration.

FIG. 7 shows an example scenario in which a hand 710 is positioned near to a linear guide that features the safety guide 600 of FIG. 6. A counterpart safety guide 602 is placed opposite the safety guide 600 such that each guide has an open channel facing the other guide. In the example of FIG. 7, the counterpart guide safety guide 602 has a different overall shape or form factor to the safety guide 600. In some examples, the counterpart safety guide 602 is of the same form as the safety guide 600 and in other examples the counterpart safety guide 602 may not be present at all. The patient support apparatus 310 is configured or programmed so that the patient support surface 312 moves in the direction of the arrow labelled X. FIG. 8 shows a subsequent position of the patient support apparatus 310 after the patient support surface has moved in the direction of the arrow labelled X.

Compared to the similar scenario shown in FIG. 5, in FIGS. 7 and 8 the finger trap possibility has been removed by the use of the safety guide 600 of FIG. 6. The open channel 610 has a surface that, when placed alongside the linear guide, exhibits a smooth transition of profile instead of the abrupt change in profile present in FIG. 5. The cross sectional profile of open channel varies smoothly so that, at the end of the channel adjacent to the linear guide, the profile of the channel matches a profile of the bearing guide, so that something moving along either surface will experience the transition between surfaces as a continuous or near-continuous surface. The open channel 610 thus provides a guiding effect to the hand 710 that guides or pushes the hand away from the linear guide and avoids any pinching, particularly when the linear guide is in operation with moving parts. In particular, the open channel 610 of the safety guide 600 may be for guiding a human finger away from the elongate bearing guide. Instead of presenting two interfaces between which a finger or digit of the hand 710 can become trapped, as per the end stops 420, 430 of FIGS. 4 and 5, the safety guides 600, 602 of FIGS. 7 and 8 each present an open channel 610 that guides the fingers of the hand 710 out of the channel and away from the linear guide as the patient support surface moves, thereby reducing and/or removing the risk of finger trapping.

The open channel 610 is hence arranged so that, when a human finger is present in the open channel 610 at a point where the channel has a first depth and the finger is pushed in a direction parallel to the translation axis and away from the elongate bearing guide, the human finger is guided along the surface to a point where the channel has a second depth, wherein the second depth is shallower than the first depth.

The safety guide 600 may guide the hand 710 away from the linear guide in a direction perpendicular to the direction of motion X of the linear guide and/or in a direction opposite to that of the direction of motion X of the linear guide. In FIG. 7 and FIG. 8, two safety guides 600, 602 are used, but a single guide may be used to achieve the effect of guiding the hand of a user away from the linear guide.

The elongate bearing guide 420 of the linear guide may be shaped with similar or identical depths, widths, and/or shapes to the open channel 610 in order to likewise prevent a finger of the hand 710 being caught in the elongate bearing guide, but need not always be. The use of the safety guide 600 at the end of the linear guide prevents fingers from being jammed, and, in examples wherein a continuous channel, groove, or elongate opening is formed by the surface of the open channel 610 and a guide surface of an elongate bearing guide, the continuous channel or groove will also guide the fingers of the hand 710 away from the interface between the two parts.

The safety guide 600 need not be restricted to use only on a particular linear guide of the patient support system and may be applied to other parts of the patient support system where a finger trap risk is present, thereby improving the safety of the system.

The safety guides 600, 602 may also each provide a stopping interface that functions in a similar manner to the stopping interface of FIGS. 4 and 5. In particular, each safety guide 600, 602 is arranged in a way that impedes the passage of a bearing moving within the respective elongate bearing guide.

Figure 9:
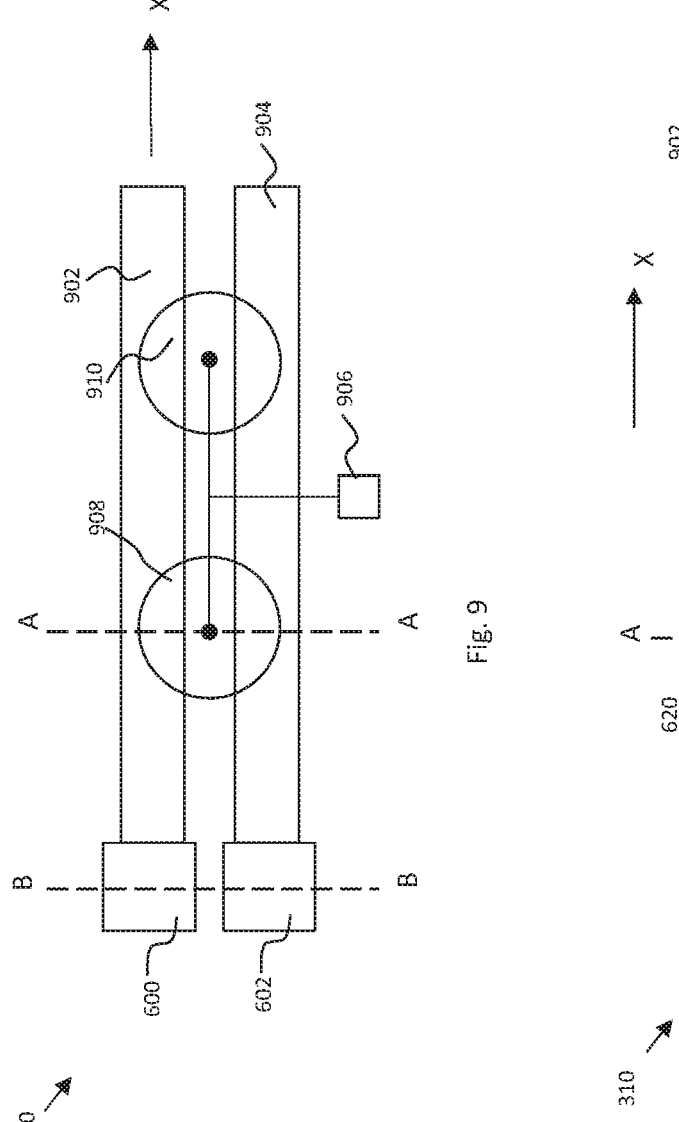
FIG. 9 shows a schematic of a linear guide for a patient positioning apparatus in a first configuration.
Figure 10:
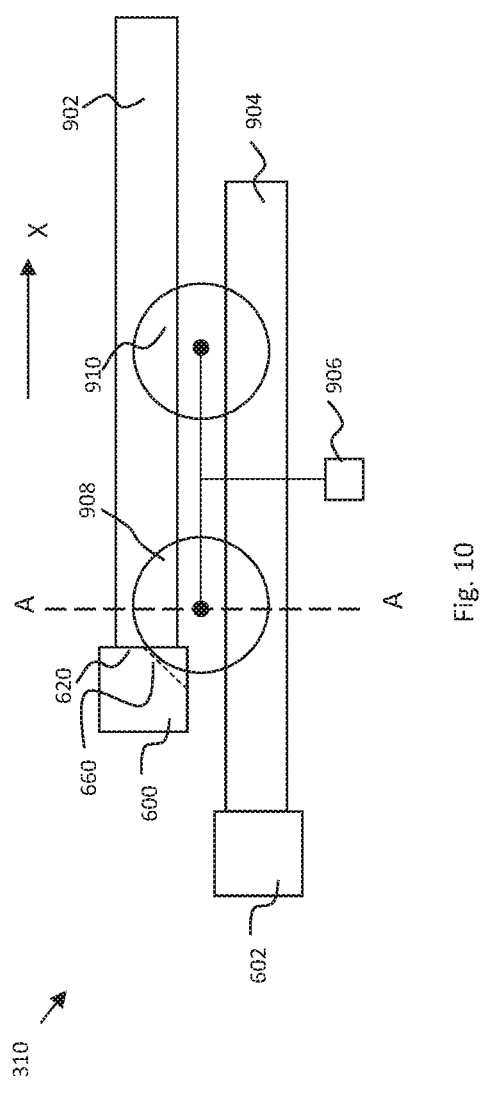
FIG. 10 shows the linear guide of FIG. 9 in a second configuration.

FIGS. 9 and 10 show a schematic of a linear guide that may be used in place of any of the linear guides described herein. Two elongate bearing guides 902, 904 hold two bearings 908, 910, which are attached to a carriage 906. As will be appreciated by those skilled in the art, instead of two bearings, any other number of one or more bearings may be used. Furthermore, the one or more bearings may be attached or mounted to either, or neither, of the two moveable components 902, 904 that are positioned on either side of the linear guide.

The elongate bearing guides 902, 904 are respectively attached to one of the intermediate support structure 313 and the patient support base supporting structure 315. The first elongate bearing guide 902 is moved in the direction marked with an arrow labelled X as the patient support surface is translated relative to the patient support base.

When the first elongate bearing guide 902 reaches a particular point relative to the second elongate bearing guide 904, as shown in FIG. 10, the bearing 908 nearest to the safety guides 600, 602 presses against the safety guide 600 attached to the first elongate bearing guide 902. In doing so, the bearing 802 is prevented by the safety guide 600 from moving beyond an end position of the translational motion along the translation axis of the linear guide. Depending upon the profile used for the open channel in the safety guide 600, the bearing 908 may contact the safety guide 600 differently. In some examples, the bearing 908 simply presses against the face 620 of the safety guide 600 that faces the bearing 908 and is prevented from moving further in that direction. In other examples, such as when the surface 660 of the open channel is aligned with the bearing contact surface of the elongate bearing guide, the bearing 908 may partially enter the open channel and come into contact with the surface 660 of the open channel as the open channel narrows in depth and/or width.

Figure 12:
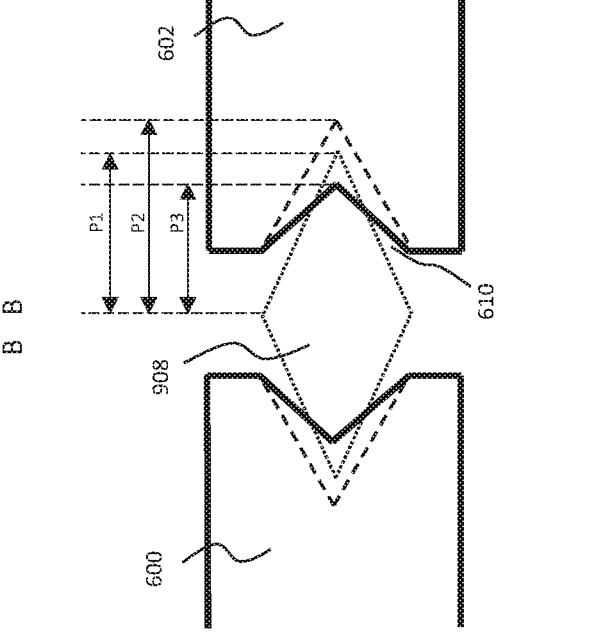
FIG. 12 shows a cross-section of the linear guide of FIGS. 9 and 10.
Figure 11:
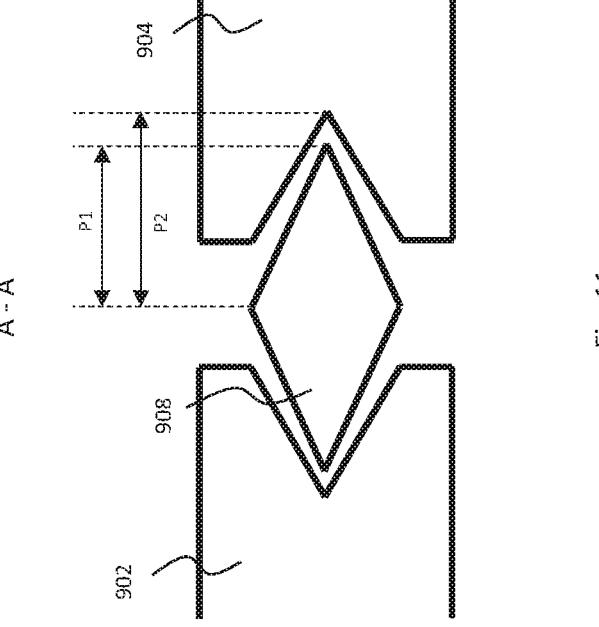
FIG. 11 shows a cross-section of the linear guide of FIGS. 9 and 10.

Such an example is shown in FIG. 10, with a dashed line showing a simplified depiction of the surface 660 of the open channel which is in contact with, and acts to stop, bearing 908. FIGS. 11 and 12 show cross-sectional views of the linear guide of FIGS. 9 and 10. A cross-section taken along the dashed line A-A of FIG. 9 is shown in FIG. 11 and a cross-section taken along the dashed line B-B is shown in FIG. 12. In the cross-section along the line A-A, the two elongate bearing guides 902, 904 are shown and a cross-section of the bearing 908 is shown. The bearing has a depth from its centre to edge that is labelled with the double-headed arrow P1. The bearing allows the elongate bearing guides 902, 904 to move relative to each other. The right-hand elongate bearing guide 904 has a guide surface that defines a V-shaped groove that has a depth running perpendicular to the long axis of the elongate bearing guide. The guide surface is hence arranged to accommodate the bearing 908 and any other bearings used in the linear guide. In some examples, the guide surface of the elongate bearing guide may form an elongate channel with a different profile, such as similar or identical profiles to those of the open channel 610 described above. The channel or groove formed by the guide surface allows the bearing to pass along the elongate bearing guide 904 and has a depth P2 defined relative to the centre of the bearing. There is a similar channel present in the other elongate bearing guide 902, as shown in the cross-section A-A.

The cross-section along the line B-B shows the effect of placing the safety guides 600, 602 at the end of the elongated bearing guides. The position of the bearing 908 within the channels formed by the guide surfaces of the elongate bearing guides is shown with dashed lines and depths P1 and P2 from cross-section A-A are also shown. The safety guide 602 on the right-hand side is provided with an open channel 610, as is the safety guide 600 on the left-hand side (not labelled). The open channel 610 has a depth at a particular point along its length that has a depth relative to the centre line of the bearing that is labelled with the double-headed arrow P3. The depth P3 is smaller than the depth of the bearing P1, so that the bearing is unable to pass beyond the safety guides 600, 602 and its movement is impeded. Each safety guide 600, 602 is therefore arranged to limit the extent of the translational motion of the bearing along the translation axis.

Such an arrangement is beneficial in multiple ways. For example, the safety guide 600 can assist in manufacturing the linear guide, and in particular can assist in mounting and coupling the components by containing the bearing within the elongate bearing guide and preventing it from moving out of the end of the elongate bearing guide. By using a safety guide 600 at each end of one or more elongate bearing guides, one or more bearings can be confined within the elongate bearing guide(s). When the patient support surface is translated, the safety guide prevents further motion of the one or more bearings in the direction towards the safety guide. Confining the bearing in this way prevents over-extension of the movement of the patient support surface and prevents the patient support surface from becoming decoupled from the patient support base and vice versa. That is particularly the case for arrangements wherein a bearing is contained between two elongate bearing guides, as depicted in FIGS. 9-12.

Advantageously, the one or more bearings being contained within the linear guide by the safety guide 600 means that, should a bearing become erroneously detached from its mount during operation of the linear guide, the bearing cannot fall out of the linear guide altogether—which could cause catastrophic decoupling of the intermediate support structure 313 and the supporting structure 315.

To provide a stopping effect on a bearing, the interface between the safety guide 600 and the elongated bearing guide can take several forms. As described above, a continuous channel may run along the elongate bearing guide and the safety guide 600. In such an arrangement, although part of the bearing may be moveable into the safety guide 600, as the depth and/or width of the safety guide 600 narrows or tapers, there will be a point at which the bearing cannot move any further and is prevented from doing so. Whichever arrangement is used, the safety guides 600, 602 can effectively limit the extent of movement possible with the linear guide.

A similar finger trap risk to that described above is associated with other stop components of the patient support system. In particular, in one approach a moveable stop is attached to a brake belt which moves within a single, wide elongate gap in the underside of the supporting structure 315 of the patient support base. A significant finger trap risk can be present when the moveable stop reaches either end of the elongate gap, whereby a finger, thumb, hand, or other appendage may be trapped or crushed between the moveable stop and the supporting structure.

Figure 13:
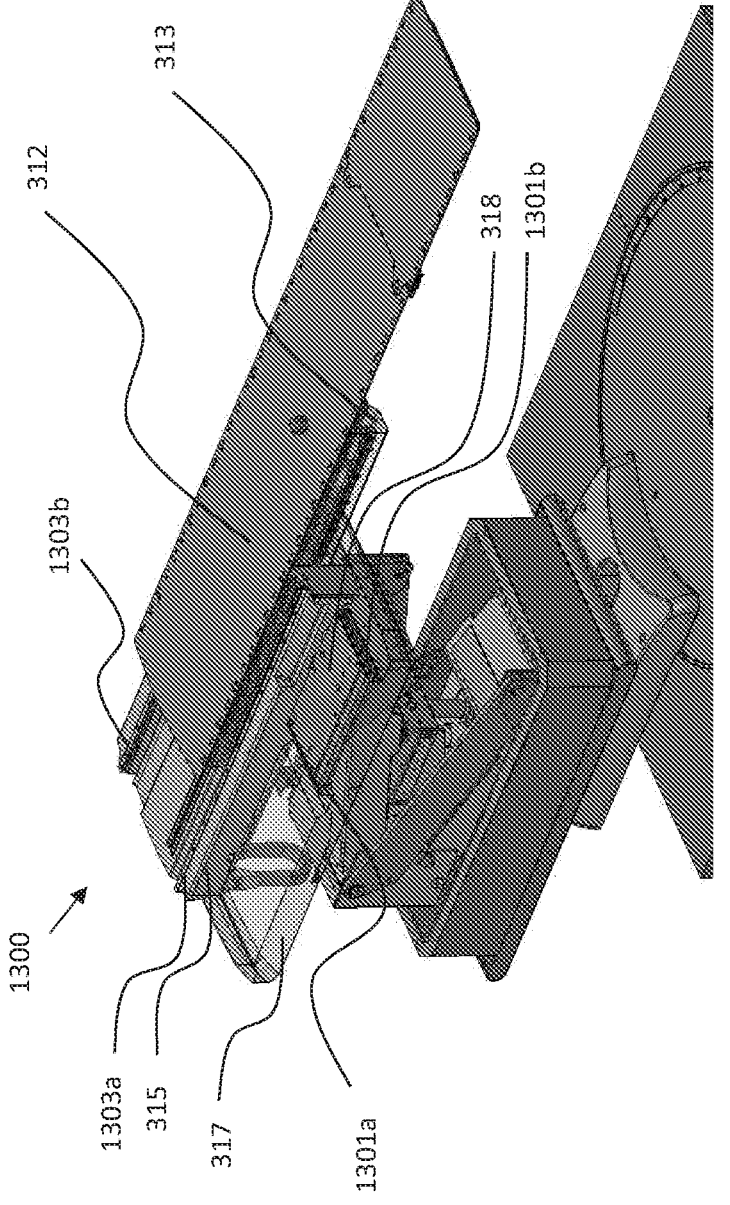
FIG. 13 shows a patient positioning apparatus in a first configuration.

FIG. 13 shows a patient support apparatus 1300. The patient support apparatus 1300 is based on the patient support apparatus 300 of FIGS. 2 and 3, and may function and/or be arranged and/or controlled in the manner described for the patient support apparatus 300 of FIGS. 2 and 3. Likewise, the patient support apparatus may comprise the components described herein for the examples of FIGS. 6 to 12. The patient support apparatus 1300 comprises the patient support surface 312, the intermediate support structure 313, the supporting structure 315 of the patient support base, and the lateral sledge 317.

The patient support apparatus 1300 further comprises a base member 318, which may also be referred to as a lateral translation stage. The base member 318 is mounted to the lateral sledge 317. The supporting structure 315 of the patient support base, which may also be referred to as a patient support surface carrying member 315, is coupled to the base member 318 via a linear guide mechanism which may comprise a plurality of linear guides 1301a, 1301b. The linear guide mechanism 1301a, 1301b is arranged such that it runs in a direction perpendicular to the direction of linear guides 1303a, 1303b that couple the intermediate support structure 313 to the patient support surface carrying member 315. Hence, the base member 318 is arranged such that the patient support surface carrying member 315 can be translated along a direction that is perpendicular to the direction of translation of the intermediate support structure 313 with respect to the patient support surface carrying member 315. The translation enabled by the coupling of the base member 318 and the patient support surface carrying member 315 may be referred to as lateral translation. The translation enabled by the coupling of the patient support surface carrying member 315 and the intermediate support structure 313 may be referred to as longitudinal translation. The patient support surface 312 is thus moveable in each of a lateral and longitudinal direction. In some examples, the patient support surface 312 and the patient support surface carrying member 315 may be formed of a single integral component. Each linear guide may be formed using elongated bearing guides 410, 420 and a safety guide 600 may be used for each linear guide as described herein.

Figure 14:
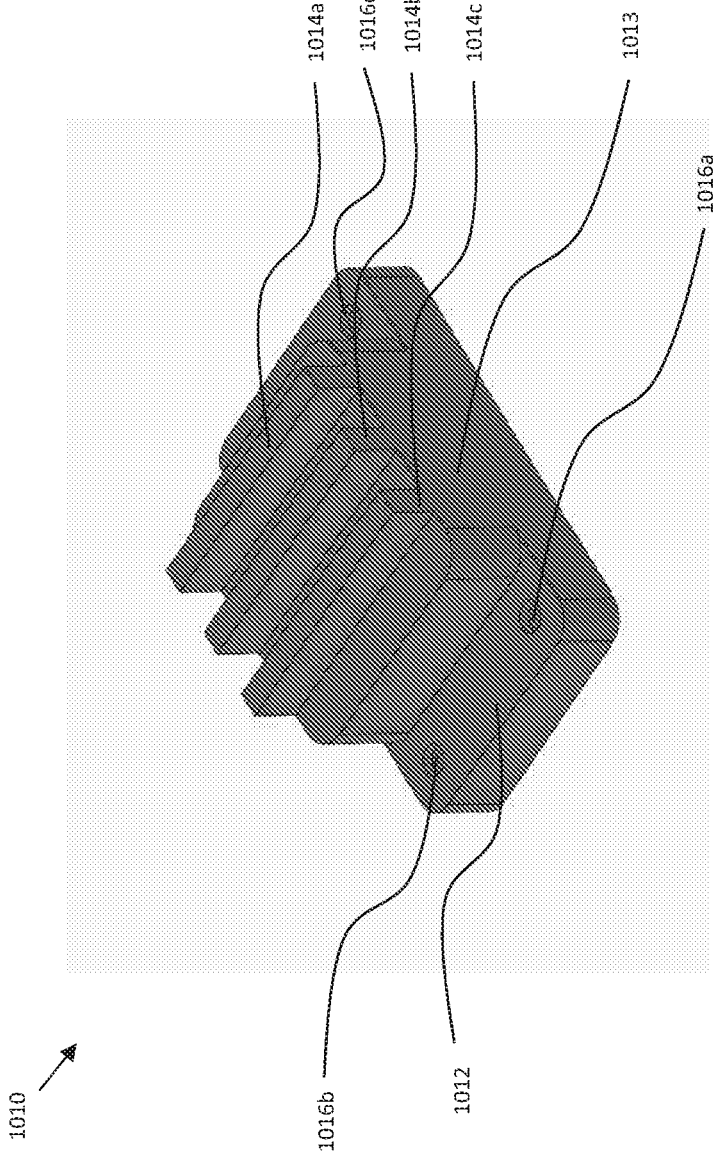
FIG. 14 shows a first stop for a patient positioning apparatus.

FIG. 14 shows a first stop 1010. The first stop 1010 has a base section 1012, a body section 1013, and three teeth 1014a-c. The first stop has threaded holes 1016a-c (and a fourth hole not shown in FIG. 13) for fixedly securing the first stop to a part of the patient support system such as the base member 318. Other configurations of holes or means for securing the first stop may be employed and/or the first stop may be integrally formed with the part of the patient support system. The body section 1013 provides the first stop with a particular height and mass. The three teeth 1014a-c extend upwards from the body section. The teeth 1014a-c are arranged with a particular height, width, and spacing. In the example of FIG. 12, three teeth are shown with equal height, width, and spacing. In other examples, any number of teeth greater than one may be used, and furthermore, they need not be of equal size, nor need be of equal spacing or equal width. The plurality of teeth 1014a-c shown in FIG. 12 are shown with a flat upper surface, but pointed or curved surfaces may alternatively or also be used. The teeth may be shaped as, and referred to as, prongs, or tines, such as that of a fork, rake, or comb. The teeth may be crenelated.

Figure 15:
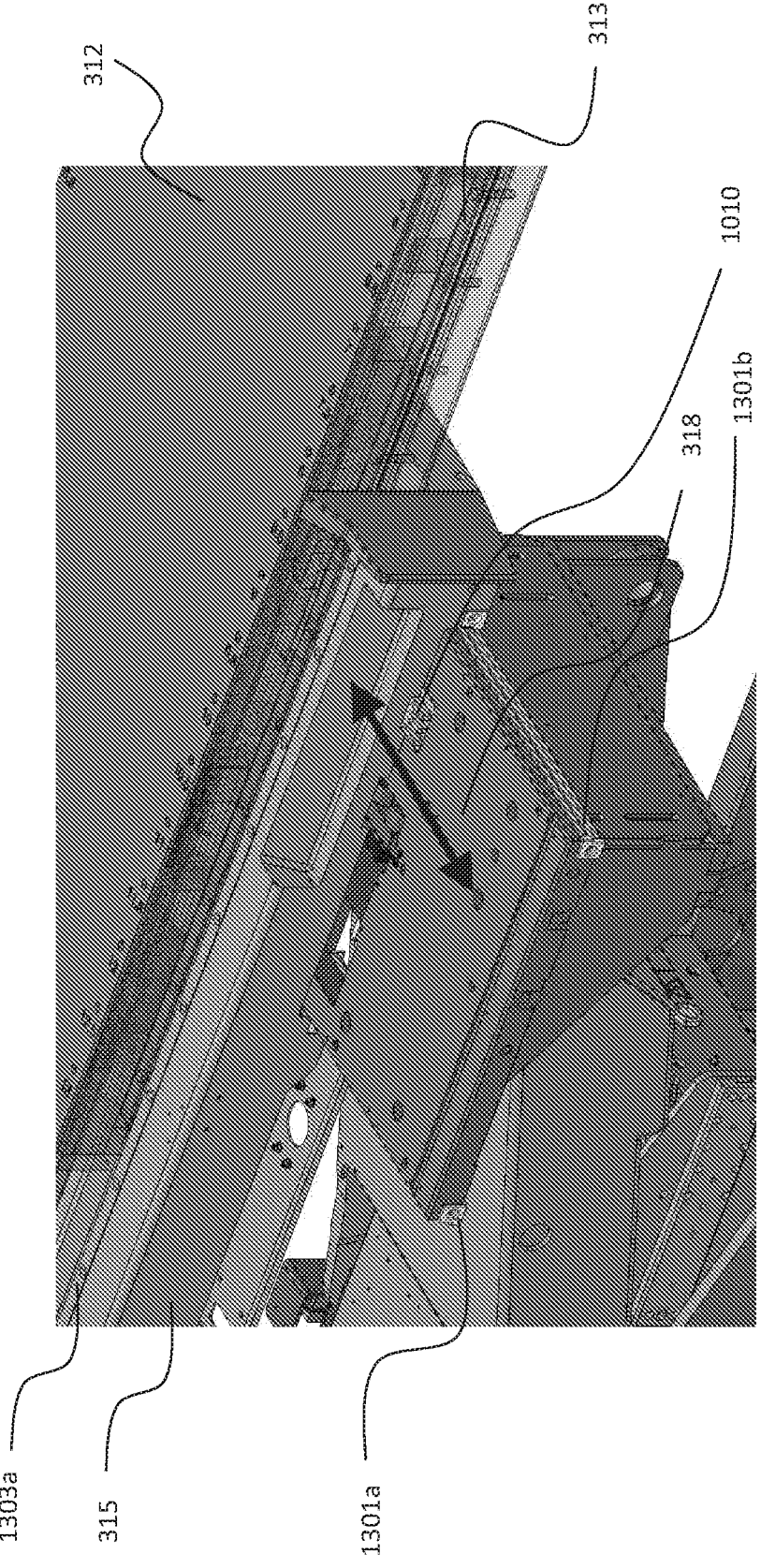
FIG. 15 shows a close up of the first stop of FIG. 14 in situ on the patient positioning apparatus of FIG. 13 in a first configuration.

FIG. 15 shows the patient positioning apparatus 1300 of FIG. 13 with the first stop 1010 mounted to the base member 318. The first stop 1010 is fixedly secured to a surface of the base member 318. The first stop is placed such that the base 1013 part of the first stop is set into the base member 318. Arranged thus, the plurality of teeth 1014a-c of the first stop 1010 protrude outwards from the surface that the first stop is 1010 is mounted to, pointing away from the base member 318 and towards the patient support surface carrying member 315.

The patient support surface carrying member 315 is provided with a plurality of elongate slots in the surface of the patient support surface carrying member 315 that faces the base member 318. Another, opposite surface of the patient support surface carrying member 315 is arranged to carry the patient support surface 312, which may be carried via the intermediate structure 313. The plurality of elongate slots is arranged such that a long axis of each slot runs parallel to the direction of translation of the patient support surface member 315 relative to the base member 318, referred to above as lateral translation and achieved using the linear guides 1301a, 1301b. Each of the plurality of teeth 1014a-c projects into a respective one of the plurality of elongate slots. Each tooth may fully or partially enter the respective slot. Each of the slots has a width, for example 8 mm. The width of each slot is similar to that of the respective tooth, which may be 1 or 2 mm smaller in width than the slot. When the patient support surface carrying member 315 is moved or translated with respect to the base member 318, or vice versa, the plurality of teeth 1014a-c translate along the long axis of the plurality of elongate slots. The plurality of teeth 1014a-c may thus be translatable back and forth along the length of the plurality of elongate slots as the movement of the patient support surface carrying member 315 progresses. In FIG. 15, the directions of this movement are shown with a double-headed arrow.

Figures 16, 17:
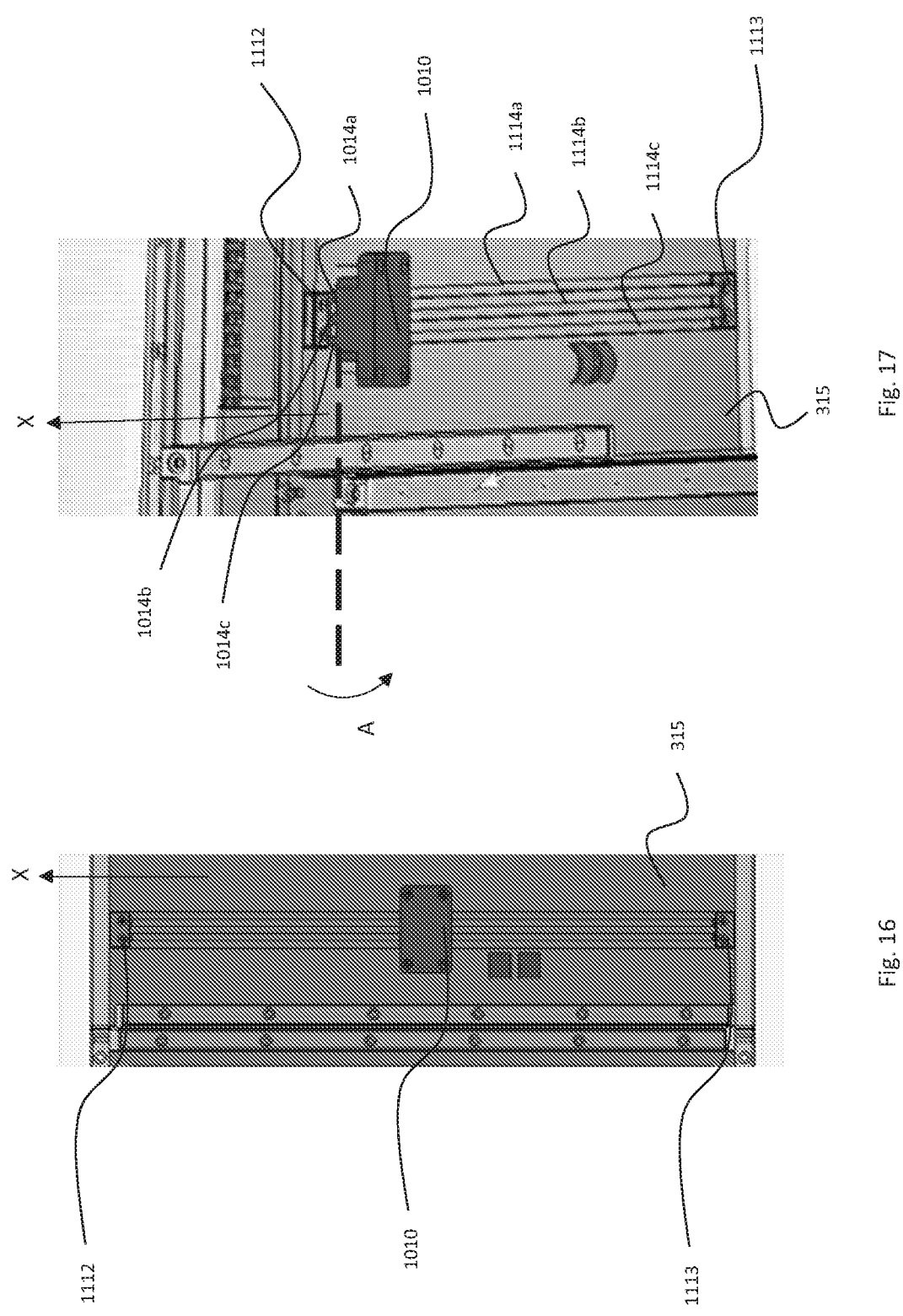
FIG. 16 shows the first stop of FIG. 14 in situ on the patient positioning apparatus of FIG. 15 in a second configuration.
FIG. 17 shows the first stop of FIG. 14 on the patient positioning apparatus of FIG. 15 in a third configuration.

FIGS. 16 and 17 show perspective views of an internal cutaway of the underside of the patient positioning apparatus 1300 of FIG. 15. FIG. 16 shows a first perspective, in which the patient positioning apparatus is positioned prior to relative motion of the first stop 1010 in the direction of the arrow labelled X. FIG. 17 shows a second perspective in which the patient positioning apparatus is positioned after undergoing relative motion of the first stop 1010 in the direction of the arrow labelled X. As described above in relation to FIG. 15, the underside of the patient support surface carrying member 315 is provided with a plurality of elongated slots 1114a-1114c running along the length of the patient support surface carrying member 315. The number of slots corresponds to the number of teeth on the first stop 1010, which is three in this example. Each tooth is arranged and sized such that it can pass into and/or through a respective slot. In FIG. 17, the representation of the first stop 1010 has been rotated out of plane according to the curved arrow marked A in order to show the interaction of the teeth 1014a-1014c with the slots 1114a-1114c.

The first stop 1010 is thus arranged to be moveable through the length of the plurality of elongated slots 1114a-1114c so that when the patient support surface is translated, the first stop correspondingly moves through and along the length of the elongated slots.

At each end of the plurality of elongated slots is a second type of stop 1112, 1113, which may each be referred to as a second stop or a fixed stop. Each second stop 1112, 1113 may be mounted to the patient support surface carrying member 315. Each second stop 1112, 1113 has a size that preferably spans the total combined width of the plurality of elongated slots 1114a-1114c. Each second stop 1112, 1113 is arranged laterally across the end of the plurality of elongated slots 1114a-1114c to intersect a long axis of the plurality of elongated slots 1114a-1114c. When the first stop 1010 reaches an end of the plurality of elongated slots 1114a-1114c, the first stop 1010 will meet a respective one of the second stops 1112, 1113 and will press against the respective second stop, such that that second stop 1112, 1113 blocks any further translation of the first stop 1010. Each tooth 1014a-1014c of the first stop 1010 presses against, or contacts, the second stop 1112, 1113. The first stop 1010 hence exerts a force on the second stop, and vice versa, that is distributed over each tooth. Each second stop is fixed in place such that the first stop 1010 is impeded from passing beyond the second stop, limiting the range of motion of the patient support surface carrying member 315 relative to the base member 318. The point at which the first stop 1010 reaches an end of the plurality of elongated slots 1114a-1114c and abuts against a second stop 1112, 1113 can be considered an end point, and may be predetermined, and/or may be adjusted according to the requirements of the patient positioning system. In some examples, only one second stop is used.

Such an arrangement functions as an end stop for lateral motion of the patient support surface carrying member 315 relative to the base member 318, preventing the linear guide from being overextended and preventing possible decoupling of the patient support surface carrying member 315 from the patient support apparatus 1300.

Figure 18:
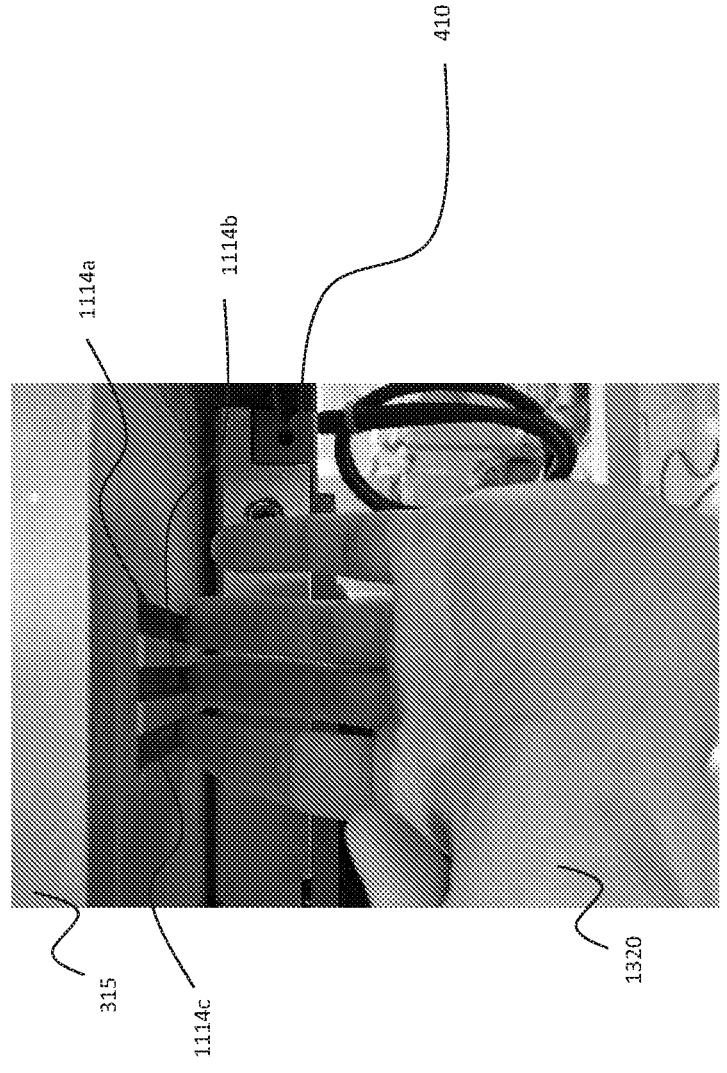
FIG. 18 shows a partial view of the underside of a patient support surface.

FIG. 18 demonstrates the reduction and/or removed finger trap risk beneficially provided by using the apparatus described herein. A hand of a user, clinician, or patient is positioned near the underside of the patient support apparatus 1300. As shown in FIG. 18, each elongated slot 1114*a*-1114*c* is sized so that a finger cannot fit into the slot and hence is less at risk from trapping or crushing if the first stop presses against the hand. For example, each slot may have a maximum width of 8 mm, and the spacing between each slot may have similar dimensions. In some examples, the width of each tooth is 1 or 2 mm smaller than the width of each slot.

The approach of using a number of narrow (relative to a human finger) teeth in conjunction with correspondingly-sized slots allows the design of the first stop to be optimised to provide a sufficiently robust stopping interface across the teeth of the first stop alongside a reduction in size of the elongated slots that it moves within, in order to reduce the risk of finger trapping and hence improve safety.

In some examples, the second stop may be shaped with teeth in a similar manner to the first stop, so that the teeth of each respective stop contact each other when the patient support surface is at the limit of its motion.

In some examples, each of the plurality of elongated slots has a width smaller than a typical human finger. In some examples, each of the plurality of elongated slots has a width that is sufficiently small that a finger, or skin, cannot be pinched between the first stop 1010 and a hard surface, such as a surface of the second stop.

In some examples, the teeth 1014*a*-*c* of the first stop 1010 may have a castellated overall profile. In some examples, the teeth 1014*a*-*c* of the first stop 1010 may have an irregular profile, and/or shape, and/or spacing. In some examples, the teeth 1014*a*-*c* of the first stop 1010 may form an overall profile like that of a comb. In some examples, the teeth 1014*a*-*c* of the first stop 1010 may instead be shaped like prongs, or tines, and be referred to as such.

The examples of the systems of FIGS. 13 to 18 may be combined with the examples of the safety guide 600 disclosed herein, and in particular those of FIGS. 6 to 12.

Systems are disclosed for patient positioning in radiotherapy. A patient support system comprises a base, a linear guide comprising a bearing and an elongate bearing guide arranged to guide translational motion of the bearing along a translation axis, and a patient support surface coupled to the base via the linear guide, the linear guide being arranged to guide linear motion of the patient support surface relative to the base in a direction parallel to the translation axis.

The patient support system comprises a safety guide having a safety guide end adjacent to one end of the elongate bearing guide, wherein an open channel defined by a surface of the safety guide starts at the safety guide end with an open part of the channel facing the translation axis, and a depth of the channel tapers away from the elongate bearing guide.

In some examples, the intermediate support structure 313 may be referred to as a carried structure and/or it may be integral with the patient support surface.

Those skilled in the art will recognise that a wide variety of modifications, alterations, and combinations can be made with respect to the above described examples without departing from the scope of the disclosed concepts, and that such modifications, alterations, and combinations are to be viewed as being within the ambit of the disclosed concepts.

Those skilled in the art will also recognise that the scope of the invention is not limited by the examples described herein, but is instead defined by the appended claims.

The invention claimed is:

1. A patient support system for a radiotherapy system, the patient support system comprising:
    a base;
    a linear guide comprising a bearing and an elongate bearing guide arranged to guide translational motion of the bearing along a translation axis;
    a patient support surface coupled to the base via the linear guide, the linear guide being arranged to guide linear motion of the patient support surface relative to the base in a direction parallel to the translation axis; and
    a safety guide having a safety guide end adjacent to one end of the elongate bearing guide, wherein an open channel defined by a surface of the safety guide starts at the safety guide end with an open part of the open channel facing the translation axis, and wherein a depth of the open channel tapers away from the elongate bearing guide.

2. The patient support system of claim 1, wherein the open channel of the safety guide is configured for guiding a human finger away from the elongate bearing guide.

3. The patient support system of claim 1, wherein the surface of the safety guide that defines the open channel is arranged so that, when a human finger is present in the open channel at a point where the open channel has a first depth and the human finger is pushed in a direction parallel to the translation axis and away from the elongate bearing guide, the human finger is guided along the surface to a point where the open channel has a second depth, wherein the second depth is shallower than the first depth.

4. The patient support system of claim 1, wherein the surface that defines the open channel is arranged to align with a guide surface of the elongate bearing guide.

5. The patient support system of claim 4, wherein the surface that defines the open channel has a substantially same cross-sectional profile as the guide surface at that end.

6. The patient support system of claim 4, wherein the surface that defines the open channel is arranged to align with the guide surface of the elongate bearing guide to form a continuous elongate opening.

7. The patient support system of claim 1, wherein the open channel has a width that tapers along a length of the open channel.

8. The patient support system of claim 1, wherein the depth of the open channel tapers linearly away from the safety guide end.

9. The patient support system of claim 1, wherein the depth of the open channel tapers to nothing.

10. The patient support system of claim 1, wherein the safety guide is arranged so that, when the bearing is moved in a direction parallel to the translation axis and reaches the safety guide, the bearing contacts the safety guide so as to prevent further motion of the bearing in that direction.

11. A patient support system for a radiotherapy system, the patient support system comprising:
    a patient support surface carrying member arranged to carry a patient support surface on a first side thereof;
    a linear guide mechanism; and a base member coupled to the patient support surface carrying member via the linear guide mechanism, wherein the linear guide mechanism is arranged to guide linear motion of the patient support surface carrying member relative to the base member in a direction parallel to a translation axis and parallel to a plurality of elongate slots in a second surface of the patient support surface carrying member, wherein the second surface of the patient support surface carrying member is opposite to the first side thereof, wherein the base member includes a first stop having a plurality of teeth, each tooth projecting into a respective one of the plurality of elongate slots, the first stop being arranged so that its teeth translate along the plurality of elongate slots when the patient support surface carrying member is moved relative to the base member in the direction parallel to the translation axis, and wherein the patient support surface carrying member includes a second stop arranged so that, when the patient support surface is moved relative to the base member in the direction along the translation axis and reaches an end point, the first stop contacts the second stop so as to prevent further motion of the patient support surface in that direction.

12. The patient support system of claim 11, wherein a width of each slot is less than or equal to 8 mm.

13. The patient support system of claim 11, wherein the second stop comprises a plurality of teeth.

14. The patient support system of claim 11, wherein the plurality of teeth of the first stop have a castellated profile.

15. The patient support system of claim 11, wherein the plurality of teeth of the first stop have a comb profile.

16. The patient support system of claim 11, further comprising the patient support surface.

17. The patient support system of claim 16 wherein the patient support surface is formed integrally with the patient support surface carrying member.

* * * * *